United States Patent [19]

Mano et al.

[11] Patent Number: 5,047,066
[45] Date of Patent: Sep. 10, 1991

[54] DYE COMPOSITION FOR KERATINOUS FIBERS CONTAINING A 2-SUBSTITUTED 4-AMINOPHENOL COMPOUND AS A DEVELOPER, AND A COUPLING SUBSTANCE

[75] Inventors: Tsutomu Mano, Saitama; Jiro Kawase, Funabashi; Daisuke Misu, Wakayama; Michio Obayashi, Toyonaka, all of Japan

[73] Assignee: Kao Corporation, Tokyo, Japan

[21] Appl. No.: 361,330

[22] Filed: Jun. 5, 1989

[30] Foreign Application Priority Data

Jun. 8, 1988 [JP] Japan ................. 63-141412

[51] Int. Cl.$^5$ .............................. A61K 7/13
[52] U.S. Cl. ........................... 8/421; 8/405; 8/408; 8/423; 8/406; 8/415; 8/410; 8/409
[58] Field of Search ................ 8/405, 406, 421, 408, 8/423, 415, 410, 409

[56] References Cited

U.S. PATENT DOCUMENTS

| | | | |
|---|---|---|---|
| 3,698,852 | 10/1972 | Pantzer ..................... | 8/412 |
| 3,861,868 | 1/1975 | Milbrada ................... | 8/10.2 |
| 3,893,803 | 7/1975 | Kaiser ....................... | 8/10.2 |
| 3,957,424 | 5/1976 | Zeffren et al. ............. | 8/10.2 |
| 4,104,021 | 8/1978 | Lapidus et al. ............. | 8/421 |
| 4,169,703 | 10/1979 | Fakhouri ................... | 8/10.2 |
| 4,321,053 | 3/1982 | Konrad et al. ............. | 8/407 |
| 4,330,291 | 5/1982 | Baguat et al. .............. | 8/406 |
| 4,333,730 | 6/1982 | Baguat et al. .............. | 8/407 |
| 4,479,803 | 10/1984 | Bachmann et al. ........ | 8/406 |
| 4,797,130 | 1/1989 | Clausen et al. ............ | 8/421 |

FOREIGN PATENT DOCUMENTS

| | | |
|---|---|---|
| 226072 | 6/1987 | European Pat. Off. |
| 2951377 | 7/1981 | Fed. Rep. of Germany. |
| 1366799 | 6/1964 | France. |
| 2352542 | 12/1977 | France. |

OTHER PUBLICATIONS

*Hawley's Condensed Chemical Dictionary*, 11th edition, Van Nostrond Reinhold Co., NY, NY 1987, p. 62.

*Primary Examiner*—Prince E. Willis
*Assistant Examiner*—J. Silbermann
*Attorney, Agent, or Firm*—Oblon, Spivak, McClelland, Maier & Neustadt

[57] ABSTRACT

A hair dyeing composition comprising a special developer and a coupling agent is disclosed. The developer is a 4-aminophenol derivative substituted at the 2-position which is represented by the following formula (I),

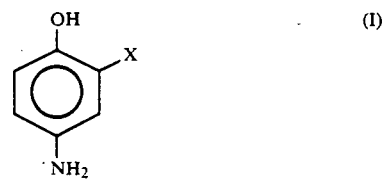

in which X represents a group —NHCOR$^1$ (R$^1$ is a linear or branched alkyl group having 1–5 carbon atoms), a group —COOR$^2$ [R$^2$ is a hydrogen atom, a linear or branched alkyl group having 1–5 carbon atoms, a monohydroxy alkyl group having 1–5 carbon atoms, a polyhydroxy alkyl group having 1–5 carbon atoms, or a group —(CH$_2$)$_n$NR$^3$R$^4$ (R$^3$ and R$^4$ individually represent a hydrogen atom or a linear or branched alkyl group having 1–5 carbon atoms, and n denotes an integer of 1–5)], a group —CONHR$^2$, a nitrile group, a group —SO$_3$R$^2$, or a group —SO$_2$NR$_2{}^2$ (R$^2$ has the same meaning as defined above and the two R$^2$s may be the same or different), or a salt thereof. The dye composition provides a high degree of saturation and vividness of colors as well as good fastness.

6 Claims, No Drawings

DYE COMPOSITION FOR KERATINOUS FIBERS CONTAINING A 2-SUBSTITUTED 4-AMINOPHENOL COMPOUND AS A DEVELOPER, AND A COUPLING SUBSTANCE

BACKGROUND OF THE INVENTION

1. Field of the Invention

This invention relates to a dye composition, and, more particularly, to a dye composition for keratinous fibers which is capable of dyeing keratinous fibers such as hairs and the like with a high degree of saturation and vividness.

2. Description of the Background

Oxidizing dyes, in which a developer and a coupling agent are employed in combination, have widely been used for dyeing keratinous fibers such as hairs or the like. These oxidizing dyes make use of the strong dyeing capability of oxidizing coloring substances which are produced by the oxidizing-coupling reaction of a developer and a coupling agent. P-phenylenediamine derivatives, diaminopyridine, 4-aminopyrazolone derivatives, hetero-cyclic hydrazones, and the like are used as the developer.

These conventional oxidizing dyes have problems in their insufficient performances in terms of saturation or vividness of colors, dyeing capability, and fastness. Development of a dye which is free from these defects has, therefore, been desired.

The present inventors have undertaken extensive studies in order to overcome the above problems in oxidizing dyes, and as a result found that the use of a specific 4-aminophenol derivative substituted at the 2-position as a developer for dyeing keratinous fibers provides a high degree of saturation and vividness of colors as well as good fastness. This finding has led to the completion of this invention.

SUMMARY OF THE INVENTION

Accordingly, an object of this invention is to provide a dye composition for keratinous fibers comprising a developer and a coupling substance, wherein said developer is a 4-aminophenol derivative substituted at the 2-position represented by the following formula (I),

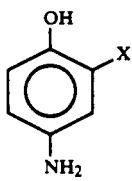
(I)

in which X represents a group —NHCOR$^1$ (R$^1$ is a linear or branched alkyl group having 1–5 carbon atoms), a group —COOR$^2$ [R$^2$ is a hydrogen atom, a linear or branched alkyl group having 1–5 carbon atoms, a monohydroxy alkyl group having 1–5 carbon atoms, a polyhydroxy alkyl group having 1–5 carbon atoms, or a group —(CH$_2$)$_n$NR$^3$R$^4$ (R$^3$ and R$^4$ individually represent a hydrogen atom or a linear or branched alkyl group having 1–5 carbon atoms, and n denotes an integer of 1–5)], a group —CONHR$^2$, a nitrile group, a group —SO$_3$R$^2$, or a group —SO$_2$NR$_2^2$ (R$^2$ has the same meaning as defined above and the two R$^2$s may be the same or different), or a salt thereof.

Other objects, features and advantages of the invention will hereinafter become more readily apparent from the following description.

DETAILED DESCRIPTION OF THE INVENTION AND PREFERRED EMBODIMENTS

Among 4-aminophenol derivatives substituted at the 2-position of the formula (I), preferable compounds for use as a developer of this invention are those having a group —NHCOR$^1$ (R$^1$ has the same meaning as previously defined), —CONHR$^{2'}$ (R$^{2'}$ is a hydrogen atom or a linear or branched alkyl group having 1–5 carbon atoms), —COOR$^{2'}$, —SO$_3$R$^{2'}$, —SO$_2$NH$_2$ or —CN for X in the formula (I).

Given as preferable examples of such compounds are 2-acetylamino-4-aminophenol, 4-amino-2-propionylaminophenol, 4-amino-2-butylylaminophenol, 4-amino-2-carbamoylphenol, 4-amino-2-(methylcarbamoyl)phenol, 4-amino-2-(ethylcarbamoyl)phenol, 4-amino-2-(propylcarbamoyl)phenol, 4-amino-2-(isopropylcarbamoyl)phenol, 4-amino-2-(butylcarbamoyl)phenol, 5-aminosalicylic acid, methyl 5-aminosalicylate, ethyl 5-aminosalicylate, propyl 5-aminosalicylate, isopropyl 5-aminosalicylate, butyl 5-aminosalicylate, 2-nitrilo-4-aminophenol, 1-hydroxy-4-aminobenzene sulfonate, methyl 1-hydroxy-4-aminobenzene sulfonate, ethyl 1-hydroxy-4-aminobenzene sulfonic acid, propyl 1-hydroxy-4-aminobenzenesulfonate, isopropyl 1-hydroxy-4-aminobenzenesulfonate, butyl 1-hydroxy-4-aminobenzenesulfonate, 1-hydroxy-4-aminobenzenesulfonamide, and the like. Among these particularly preferable compounds are 2-acetylamino-4-aminophenol, 4-amino-2-propionylaminophenol, 4-amino-2-butylylaminophenol, 4-amino-2-carbamoylphenol, 5-aminosalicylic acid, methyl 5-aminosalicylate, ethyl 5-aminosalicylate, propyl 5-aminosalicylate, butyl 5-aminosalicylate, and the like. Especially preferable compounds are 5-aminosalicylic acid and the like.

These compounds can be prepared according to known methods, e.g. methods described in Weil et al. *Chem. Ber.* 55B, 2664 (1922) (A process for the preparation of 5-amino salicylic acid), U.S. Pat. No. 2,103,552 (A process for the preparation of methyl 5-aminosalicylate), German Patent Publication No. 3,007,997 (A process for the preparation of 2-acetylamino-4-aminophenol), etc.

There is no specific restriction as to the coupling agent to be used in the dye composition of this invention. Any coupling agents conventionally used for oxidizing hair dyeing can be used for the purpose of this invention. Examples are p-amino-o-cresol, α-naphthol, o-cresol, m-cresol, 2,6-dimethylphenol, 2,5-dimethylphenol, 3,4-dimethylphenol, 3,5-dimethylphenol, benzcatechin, pyrogallol, 1,5-dihydroxynaphthalene, 1,7-dihydroxynaphthalene, 5-amino-2-methylphenol, hydroquinone, 2,4-diaminoanisole, m-toluylenediamine, 4-aminophenol, resorcin, resorcinmonomethylether, m-phenylenediamine, 1-phenyl-3-methyl-5-pyrazolone, 1-phenyl-3-amino-5-pyrazolone, 1-phenyl-3,5-diketopyrazolidine, 1-methyl-7-dimethyl-amino-4-hydroxyquinolone-2, 1-amino-3-acetyl-acetamino-4-nitrobenzole, 1-amino-3-cyanacetyl-amino-4-nitrobenzole, m-aminophenol, 4-chlororesorcin, 2-methylresorcin, 2,4-diaminophenoxyethanol, 2,6-diaminopyridine, 3,5-diaminotrifluoromethylbenzene, 2,4-diaminofluorobenzene, 3,5-diamino-fluorobenzene, 2,4-diamino-6-hydroxypyrimidine, 2,4,6-triamino-pyrimidine, 2-amino-4,6-dihydroxypyrimidine, 4-amino-2,6-dihydroxypyrimidine, 4,6-diamino-2hydroxypyrimidine, p-nitro-o-phenylenediamine, 2-amino-5-nitrophenol, p-nitro-m-phenylenediamine, o-nitro-p-phenylenediamine, 2-amino-4-nitrophenol, and the like. Especially preferable coupling agents which can afford a high degree of saturation and vividness with the proposed 4-aminophenol derivatives substituted at the 2-position are naphthols represented by the following formula (II),

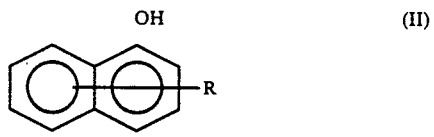

wherein R represents a hydrogen atom or a hydroxy group.

Preferable naphthols of the above formula (II) are α-naphthol, 1,5-dihydroxynaphthalene, 1,7-dihydroxynaphthalene, and 1,7-dihydroxynaphthalene-2-carboxylic acid.

A dye providing a reddish tone is important in order to satisfy a variety of needs for hair colors. According to the present invention, an excellent dye composition producing a vivid reddish hair color can be prepared by using 5-amino-salicylic acid as a developer and a naphthol having the above formula (II) as a coupling agent.

The proportion of the developer and the coupling agent to be formulated into the dye composition of this invention is approximately in the range of 1:0.5 to 1:2 in molar ratio. Excessive use of one component to the other is allowable in this range. The developers and coupling agents can be employed either independently or in combination with one or more other types of developers or coupling agents.

In addition to the above-mentioned developers and coupling agents, if necessary for producing a desired color, any known developers, coupling agents, conventional direct dyes, or the like can be formulated to the composition of this invention.

Hairs or other objects are colored by the dye composition of this invention through an oxidizing coupling reaction of the components with the aid of oxygen in the air, when the dye composition is applied to the object to be dyed. Effecting the oxidizing coupling reaction with the aid of a chemical oxidizing agent, however, is more desirable. Especially preferable oxidizing agents are hydrogen peroxide, hydrogen peroxide-adduct of urea, melamine, or sodium borate, or a mixture of one of these hydrogen peroxide-adducts and potassium peroxide-disulfate, and the like.

It is usually desirable to provide the dye composition of this invention in the form of either a cream, emulsion, gel, solution, or the like. Preparing the composition in such forms can be performed according to a conventional method. In this instance, in addition to the developers and coupling agents, various ingredients which are commonly used for cosmetics are formulated into the composition. Such ingredients include wetting agents (emulsifiers), solubilizing agents, viscosity increasing agents, stabilizers, tactile sense improvers, hair conditioning base components, perfumes, and the like. Wetting agents (emulsifiers) used in the composition include, for example, alkylbenzenesulfonates, fatty alcohol sulfates, alkylsulfonates, fatty acid alkanolamides, ethylene oxide adducts of fatty alcohol, and the like.

Given as examples of viscosity increasing agents are methyl cellulose, starch, higher fatty alcohols, paraffin oils, fatty acids, and the like. Examples of stabilizers include reducing agents such as sulfites, hydroquinone derivatives, chelating agents, and the like. Tactile sense improvers and hair conditioning base components are typified by silicones, higher alcohols, various kinds of nonionic surface active agents and cationic polymers, and the like.

The amounts of the developers plus coupling agents to be formulated into the above-mentioned form of the invented composition are 0.2 to 5% by weight, and preferably 1 to 3% by weight. Desirable amounts of the wetting agents (emulsifiers) and viscosity increasing agents in the composition is usually 0.5 to 30% by weight and 0.1 to 25% by weight, respectively.

It is desirable that the overall pH of the composition be adjusted to the range of about 8 to 10.

A typical procedure for dyeing keratinous fibers using the dye composition of this invention is now illustrated. A dye fluid is first prepared by adding an oxidizing agent to the dye composition to effect oxidizing coupling of the mixture. This dye fluid is applied to the subject keratinous fibers, which are then allowed to stand for about 10 to 50 minutes, preferably 25 to 35 minutes to effect action of the dye onto the fibers. The keratinous fibers thus sufficiently dyed are finally washed and dried. It is desirable that the temperature of the dye fluid be maintained between 15° to 40° C.

A variety of developer-coupling agent combinations are possible when using the dye composition of the present invention. Such combinations provide a wide variety of colors ranging from yellow, red, through navy blue with a high degree of color saturation and vividness. In addition, the color produced possesses excellent light resistance, washing resistance, and wear resistance. Furthermore, an excellent vivid reddish tone can be produced by using a naphthol as a coupling agent.

Other features of the invention will become apparent in the course of the following description of the exemplary embodiments which are given for illustration of the invention and are not intended to be limiting thereto.

EXAMPLES

Example 1

| Base components: | |
|---|---|
| oleic acid | 10 wt % |
| diethanolamide oleate | 8 wt % |
| oleyl alcohol | 2 wt % |
| polyoxyethyleneoctyl-dodecylether (Average EO mols: 20) | 10 wt % |
| ethanol | 15 wt % |
| propylene glycol | 10 wt % |
| ammonium chloride | 3 wt % |
| 25% aqueous ammonium | 7 wt % |
| water | 35 wt % |

100 g of the above base components were mixed with 0.01 mol of the developer and 0.01 mol of the coupling agent listed in Table 1. The mixture was adjusted to pH 9.5 with ammonia to produce dye compositions of this invention.

To 100 g of the dye composition of this invention an equivalent weight of 6% aqueous hydrogen peroxide solution was added to prepare a dye solution. This dye solution was applied to a gray human hair, and was left at 30° C. for 30 minutes. The hair was then washed with a shampoo and dried. Table 1 shows observed color tones of the dyed hairs.

Developing Agents:
P1: 2-acetylamino-4-aminophenol
P2: 5-aminosalicylic acid
P3: methyl 5-aminosalicylate Coupling Agents:
C1: p-amino-o-cresol
C2: α-naphthol
C3: m-phenylenediamine
C4: resorcin
C5: 1,5-dihydroxynaphthalene
C6: 1,7-dihydroxynaphthalene

TABLE 1

| Composition Nos. | Developers | Coupling agents | Color tone |
|---|---|---|---|
| 1 | P1 | C1 | orange |
| 2 | P1 | C2 | reddish brown |
| 3 | P2 | C3 | navy blue |
| 4 | P2 | C4 | purple |
| 5 | P3 | C1 | ochre |
| 6 | P3 | C2 | red |
| 7 | P3 | C3 | brown |
| 8 | P3 | C4 | ivory |
| 9 | P2 | C2 | red |
| 10 | P2 | C5 | purplish red |
| 11 | P2 | C6 | purplish red |

Example 2

The hair dyeing capabilities and the fastness of colors were determined on the composition Nos. 9, 10, and 11 prepared in Example 1. These performances were compared with those obtained using a comparative composition with a reddish brown color using p-aminophenol as a developing agent and p-amino-o-cresol as a coupling agent. The evaluation was made by observing the dyed hair colors after shampooing and washing with water (10 times repetition) and drying. A significant discoloration was observed on the hairs dyed with the comparative composition. On the other hand, no discoloration was recognized by the naked eye observation on the hairs dyed with the compositions of the present invention. Also, the dye compositions exhibited an excellent fastness.

Obviously, numerous modifications and variations of the present invention are possible in light of the above teachings It is therefore to be understood that within the scope of the appended claims, the invention may be practiced otherwise than as specifically described herein.

What is claimed is:

1. A dye composition for keratinous fibers, comprising a developer and a coupling substance, wherein the developer is 5-aminosalicylic acid or the methyl ester thereof or both, and the coupling agent is selected from the group consisting of 1-naphthol, 1,5-dihydroxynaphthalene, 1,7-dihydroxynaphthalene and 1,7-dihydroxylnaphthalene-2-carboxylic acid.

2. The dye composition for keratinous fibers according to claim 1, wherein said developer and said coupling agent are formulated in the dye composition in a molar ratio in the range of 1:0.5 to 1:2.

3. A dye composition for keratinous fibers, comprising a developer and a coupling substance, wherein the developer is a 4-aminophenol derivative substituted at the 2-position having the formula (I):

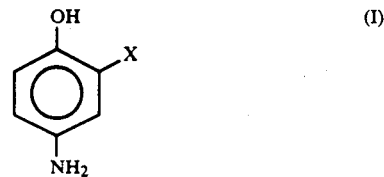

wherein X represents a group —NHCOR$^1$, wherein R$^1$ is a linear or branched alkyl group having 1 to 5 carbon atoms; an group —COOR$^2$, wherein R$^2$ is a linear or branched alkyl group having 2 to 5 carbon atoms, a monohydroxy alkyl group having 1 to 5 carbon atoms, a polyhydroxy alkyl group having 1 to 5 carbon atoms or a group —(CH$_2$)$_n$NR$^3$R$^4$, wherein R$^3$ and R$^4$ individually represent a hydrogen atom or a linear or branched alkyl group having 1 to 5 carbon atoms, and n denotes an integer of 1 to 5; a group defined above, and each R$^2$ is the same or different from the other, or a salt thereof.

4. The dye composition for keratinous fibers according to claim 3, wherein X in the formula (I) is a group —NHCOR$^1$, wherein R$^1$ is a linear or branched alkyl group having from 1 to 5 carbon atoms; —CONHR$^2'$; —SO$_3$R$^2'$, wherein R$^2'$ is a hydrogen atom or a linear or branched alkyl group having 1 to 5 carbon atoms; —SO$_2$NH$_2$ or —CN.

5. The dye composition for keratinous fibers according to claim 3, wherein said developer and said coupling agent are formulated in the dye composition in a molar ratio in the range of 1:0.5 to 1:2.

6. The dye composition for keratinous fibers according to claim 3, wherein said 4-aminophenol derivative substituted at the 2-position is a compound selected from the group consisting of 2-acetylamino-4-aminophenol, 4-amino-2-propionylaminophenol, 4-amino-2-butylylaminophenol, 4-amino-2-carbamoylphenol, 5-aminosalicylic acid, methyl 5-aminosalicylate, ethyl 5-aminosalicylate, propyl 5-aminosalicylate, and butyl 5-aminosalicylate.

* * * * *